United States Patent [19]

Shibata et al.

[11] Patent Number: 4,830,752

[45] Date of Patent: * May 16, 1989

[54] SEPARATION AGENT COMPRISING 1,3-GLUCAN

[75] Inventors: Tohru Shibata; Hajime Namikoshi; Ichiro Okamoto, all of Himeji, Japan

[73] Assignee: Daicel Chemical Industries, Ltd., Sakai, Japan

[*] Notice: The portion of the term of this patent subsequent to Nov. 22, 2006 has been disclaimed.

[21] Appl. No.: 8,114

[22] Filed: Jan. 23, 1987

Related U.S. Application Data

[63] Continuation of Ser. No. 716,734, Mar. 27, 1985, abandoned.

[30] Foreign Application Priority Data

Mar. 30, 1984 [JP] Japan .................................. 59-62661

[51] Int. Cl.$^4$ .............................................. B01D 15/08
[52] U.S. Cl. .................................... 210/635; 210/656; 210/198.2; 210/502.1
[58] Field of Search ..................... 210/635, 656, 198.2, 210/502.1; 55/67, 386

[56] References Cited

U.S. PATENT DOCUMENTS

| | | | |
|---|---|---|---|
| 3,597,350 | 8/1971 | Determann | 210/656 |
| 4,111,838 | 9/1978 | Schaeffer | 210/656 |
| 4,143,201 | 3/1979 | Miyashiro | 210/635 |

OTHER PUBLICATIONS

Chemical Abstracts 85:122713k, vol. 85, 1976, p. 549.
Chemical Abstracts 100:16959p, vol. 100, 1984, p. 663.
Optical Resolution on Polymer by Okamoto, a publication presented to the 49th Annual Meeting of the Chemical Society of Japan, Mar. 10, 1984.

*Primary Examiner*—Ernest G. Therkorn
*Attorney, Agent, or Firm*—Flynn, Thiel, Boutell & Tanis

[57] ABSTRACT

1,3-glucan is effective to separate a compound from a mixture containing the same, in particular for the optical resolution.

12 Claims, No Drawings

SEPARATION AGENT COMPRISING 1,3-GLUCAN

This application is a continuation of U.S. Ser. No. 716,734, filed Mar. 27, 1985, now abandoned.

The invention relates to a separation agent which comprises 1,3-glucan or a derivative thereof and an optional carrier. The separation agent of the invention is useful for separation of various chemical substances, especially optical resolution of optical isomers. In addition, it serves for separation of geometrical isomers and polymers having different molecular weight ranges from each other. They have not easily been separated in the state of the art.

As is well-known, optical isomers usually exhibit different effects on the living organism, though they are chemically identical to each other. Therefore, in order to improve the effectiveness of a medicine or an agricultural chemical per a unit dose or to prevent side effects or damage caused by it in the fields of medicines, agricultural chemicals and biochemistry-related industries, the preparation of optically pure compounds is an important task.

Although a preferential crystallization method or a diastereomer method has heretofore been used to perform separation between optical isomers, optical resolution, these methods are applicable to rather limited kinds compounds and frequently require a long time and much labor. Therefore, there has been a demand for a technique for effecting the optical resolution by a more practical chromatographic method.

Studying optical resolution by chromatography have long been made. However, it has been difficult to apply resolving agents developed heretofore satisfactorily to the optical resolution of all of the compounds, because there are various problems in that they have poor resolution efficiencies, that compounds to be resolved must have special functional groups, and that the resolving agents have poor stability.

It is therefore an object of the present invention to provide a resolving agent which has a chemical structure different from those of the existing resolution agents and, therefore, has resolution characteristics different from those of the latter or has a higher discriminating power for optical isomers.

In the present invention the above object can be attained by utilizing a resolving agent comprising a 1,3-glucan or its derivative as an effective component. This resolving agent exhibits different adsorptive powers for optical isomers of a certain compound.

The effective component of the resolving agent of the present invention is a polysaccharide mainly composed of the structural elements of anhydroglucose polymerized in the bonding and linkage way as shown by the following formulas or its derivative in which hydrogen atoms of the hydroxyl groups are replaced by certain atomic groups:

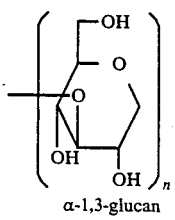

α-1,3-glucan

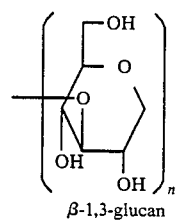

β-1,3-glucan

Although, as shown above, there are α-1,3 and β-1,3-glucans, the latter is widely distributed in nature. An example of an α-1,3-glucan is one extracted from the cell walls of *Polyprus tumulosus*. Examples of β-1,3-glucans include lentinan extracted from *Cortinellus shiitake*, pachyman from *Pachyma hoelen*, scleroglucan from genus Sclerotium, schizophyllan from *Schizophyllum commune* Fr., laminarin from Laminariaceae, paramylon from *Euglena gracilis*, and curdlan from *Alcaligenes faecallis* var. mixogens (K strain), and there is still a possibility of discovery of new β-1,3-glucans hereafter. Among these, preferable is β-1,3-glucan, in particular ones which are substantially free of side chains or lowly branched and does not contain any type of a structure other than β-1,3-structure. This is called as curdlan. In other words, β-1,3-glucan is preferred to have not more than one side chain per 10 anhydroglucose units. The number of side chains can be measured by subjecting a compound to be measured to the Hakomori methylation process, decomposing the product with an acid to produce glucose ethers and measuring a content of 2,3,6-trimethyl glucose. When 2,3,6-trimethyl glucose is obtained with yield of 90% or above, the tested β-1,3-glucan is found to fall within the above mentioned range. The branched curdlan has a substituent for hydroxyl group, such as a pyranose ring. A structure of glucan other than β-1,3-glucan is preferably contained only at 10% or below on the average, based on the total number of anhydroglucose units. It is noted that the term, curdlan, includes all pure β-1,3-glucans. A reference is made to Atsuya Harada et al., New Food Industry, 20(10), 49, and Kaname Sugimoto, Kobunshi, 26, 93(1977).

It is preferred that the degree of polymerization of said polysaccharide or its derivative is at least 5, preferably at least 10 and that it does not exceed 500 because of ease of handling, though there is no special upper limit.

Although the 1,3-glucan derivatives of the present invention may be any one which can be obtained by replacing hydrogen atoms of their corresponding polysaccharides with any substituents, so-called trisubstituted derivatives in which at least 85% of the total hydroxyl groups present in said polysaccharide are replaced with substituents of the same kind are preferable. The types of chemical bonding of the substituents may be those which are stable under the condition of use, such as ester bonds, ether bonds, thioester bonds, and urethane bonds, and the substituents may be inorganic an organic atomic groups, but those having at least one multiple bond or linkage are preferable. The organic group is preferably an aliphatic group having 2 to 10 carbon atoms, an alicyclic group having 4 to 10 carbon atoms, more preferably 4 to 7 carbon atoms, an aromatic group having 6 to 20 carbon atoms and a heteroaromatic group having 4 to 20 carbon atoms. The hydroxyl group may be free. Moreover it may esterified, etherified or carbamoylated to an extent such that the agent may maintain the ability of the optical resolution.

The polysaccharide derivatives of the present invention can be easily obtained by treating, after a suitable pretreatment, if necessary, the corresponding polysaccharides with acid halides, acid anhydrides, acid/dehydrating agent mixtures, or the like when esters or thioesters are desired. When ethers are desired. it is a general preparative method that said polysaccharides are treated with a strong base and a corresponding halide, tosylate or the like, or treated with an electrophilic unsaturated compound in the presence of a base. When urethanes are desired, they can be easily obtained by reacting said polysaccharides with the corresponding isocyanate in the presence of a Lewis base or acid catalyst.

When the resolving agent of the present invention is used in resolving a compound or its optical isomers, it is a general practice to resort to chromatographic means such as gas chromatography, liquid chromatography, or thin layer chromatography, but it is also possible to perform membrane separation.

When the resolving agent of the present invention is applied to liquid chromatography, use is made of methods such as one in which the agent in the form of powder is packed in a column, one in which the agent is applied to a capillary column as a coating, one in which the agent is formed into capillaries to utilize their inside walls, and one in which the agent is spun into fiber and a bundle of the fibers is used as a column. Among these methods, the powder method is most general. When said resolving agent is formed into powder, it is preferably to grind it or to form into beads. Although the particle size varies with the size of a column or a plate used, it is 1 μm to 10 mm, preferably 1 μm to 300 μm, and it is preferable that the particles are porous.

In order to improve the pressure durability of the resolving agent, to prevent its swelling or shrinkage caused by solvent replacement, and to improve the number of theoretical plates, it is preferable to support said resolving agent on a carrier. Although the suitable size of a carrier varies with the size of a column or a plate used, it is generally 1 μm to 10 mm, preferably 1 μm to 300 μm. The carrier is preferably porous, and the average pore diameter is 10 Å to 100 μm, preferably 50 Å to 50,000 Å. The amount of said resolving agent supported is 1 to 100 wt. %, preferably 5 to 50 wt. %, based on the carrier.

The method for supporting said resolving agent on a carrier may be a chemical or physical one. Examples of the physical methods include one comprising dissolving said resolving agent in a solvent in which the agent is soluble, thoroughly mixing the solution with a carrier, and distilling off the solvent from the mixture by evacuation or passing an air stream with heating and one comprising dissolving said resolving agent in a solvent in which the agent is soluble, thoroughly mixing the solution with a carrier, and dispersing the mixture by agitation in a liquid incompatible with said solvent to diffuse said solvent into the liquid. When crystallizing said resolving agent supported on the carrier in this way it is possible to treat it by, for example, heating. It is also possible to modify the state of supporting and, in its turn, its resolving power.

The carriers which can be mentioned include porous organic and inorganic carriers, among which the latter is preferable. Examples of the porous organic carriers which can be suitably used include high-molecular substances such as polystyrene, polyacrylamide, and polyacrylate. Examples of the porous inorganic carriers which can be suitably used include synthetic and natural substances such as silica, alumina, magnesia, titanium oxide, glass, silicates, and kaolin, and it is possible to subject them to a surface treatment to improve their affinities for said resolving agent. Examples of the surface treatments include a silane treatment in which an organosilane is used and a surface treatment by plasma polymerization.

There is no particular limitation on developing solvents which are used in performing liquid chromatography or thin layer chromatography, except that those liquids which dissolve said resolving agent or react therewith must be excluded. Since the resolution characteristics of compounds or optical isomers are, of course, influenced by a developing solvent used, it is desirable to select a suitable developing solvent according to the purpose.

In performing thin layer chromatography, it is desirable to coat a support with a 0.1–100 mm-thick layer comprising said resolving agent in the form of particles of a diameter of 0.1 μm to 0.1 mm, and, if necessary, a small amount of a binder.

When performing membrane separation, the resolving agent is used in the form of hollow yarn or film.

The resolving agent of the present invention comprising a 1,3-glucan as a principal component is effective for separation of a variety of compounds, and especially extremely effective for the resolution of optical isomers which are heretofore very difficultly separated. One of the optical isomers of a compound to be resolved will be adsorbed more strongly on the resolving agent of the present invention.

That the resolving agent of the present invention can show a marked effect will be clearly understood by making a comparison between a separation factor ($\alpha$) of an optical isomer obtained by using a resolving agent comprising curdlan triacetate shown in Example 2 as an effective component and an $\alpha$ value obtained by using a resolving agent comprising cellulose triacetate prepared in a similar manner as an effective component.

Although the reason why curdlan triacetate can exhibit such a marked discriminating power for optical isomers is not clear, it will be understood that it is associated with the fact that a 1,3-glucan has a bent molecular chain and easily takes an optically active helical form, while the cellulose molecules tend to take a relatively straightened form.

The present invention will now be described in detail with reference to examples, but it should be noted that the present invention is by no means limited thereto. The definitions of the terms used in the examples are as follows:

$$\text{capacity ratio } (k') = \frac{\left(\begin{array}{c}\text{retention volume} \\ \text{of enantiomer}\end{array}\right) - (\text{void volume})}{(\text{void volume})}$$

$$\text{separation factor } (\alpha) = \frac{\left(\begin{array}{c}\text{capacity ratio of enantiomer} \\ \text{adsorbed more strongly}\end{array}\right)}{\left(\begin{array}{c}\text{capacity ratio of enantiomer} \\ \text{adsorbed less strongly}\end{array}\right)}$$

$$\text{resolution } (Rs) = \frac{2 \times \text{(distance between peaks of more strongly adsorbed enantiomer and more weakly adsorbed enantiomer)}}{\text{total of band widths of both peaks}}$$

SYNTHESIS EXAMPLE 1

10 g of silica beads (LiChrospher SI 1000, a product of Merck Co.) were placed in a 200-ml side-arm, round-bottomed flask, and dried in vacuo at 120° C. for three hours on an oil bath. $N_2$ was blown into the flask. 100 ml of toluene which had been distilled together with $CaH_2$ was added to the silica beads. 3 ml of diphenyldimethoxysilane (KBM 202, a product of Shin'etsu Chemical Co.) was added thereto and stirred, and the mixture was reacted at 120° C. for one hour. After distilling 3 to 5 ml of the toluene, the mixture was further reacted at 120 C. for two hours. The reaction product was filtered through a glass filter, washed with 50 ml of toluene three times and then with 50 ml of methanol three times, and dried in vacuo at 40° C. for one hour.

About 10 g of said silica beads were placed in a 200-ml side-arm, round-bottomed flask, and dried in vacuo at 100° C. for three hours. After the pressure was returned to atmospheric pressure and the temperature was lowered to room temperature, $N_2$ was blown thereinto. 100 Ml of distilled toluene was added to the dried silica beads. After adding one ml of a trimethylsilylating agent, N,O-bis(trimetylsilyl)acetamide, the mixture was reacted at 115° C. for three hours. The reaction product was filtered through a glass filter, washed with toluene, and dried in vacuo for about four hours.

SYNTHESIS EXAMPLE 2

2.0 g of curdlan (a product of Wako Pure Chemicals Co., biochemical grade) was dispersed in 30 ml of water and swollen by heating it to 50° to 60° C., and 50 ml of acetic acid (a product of Kanto Chemical Co., guaranteed reagent) was added thereto. The precipitated curdlan was filtered and collected with a glass filter and washed repeatedly with acetic acid. 20 ml of the acetic acid-swollen curdlan thus produced was dispersed in a mixture of 20 ml of acetic acid, 20 ml of acetic anhydride, and 0.2 ml of 70% perchloric acid, and kept at 50° C. for 7.5 hours. During this period, each 10 ml of acetic anhydride was added after 5 and 6 hours. 0.5 ml of pyridine was added to the formed solution and the whole was poured into ice-water. The formed curdlan triacetate was precipitated, filtered through a glass filter and washed with methanol. The product weighed 2.17 g. Its infrared spectrum had an absorption $\nu_{C=O}$ at approximately 1740 cm$^{-1}$, an absorption $\nu_{C-O-C}$ of an acetate group at 1210 cm$^{-1}$, and an absorption of an ether bond of a glucose ring at 1040 cm$^{-1}$, but an absorption ascribable to $\nu_{OH}$ at approximately 3400 to 3600 cm$^{-1}$ was extremely weak, suggesting that it was a trisubstitution product.

EXAMPLE 1

1.2 g of the curdlan triacetate synthesized in Synthesis Example 2 was dissolved in a mixture of 7.0 ml of dichloromethane and 0.5 ml of methanol and filtered through a glass filter (G3). About 7.5 ml of the filtrate was mixed with 3.2 g of the silica gel particles prepared in Synthesis Example 1, and the solvent was distilled off in vacuo to obtain a powdery supported product.

APPLICATION EXAMPLE 1

Silica beads carrying the curdlan triacetate obtained in Synthesis Example 2 were packed by a slurry method into a stainless column 25 cm in length and 0.46 cm in inside diameter. A high performance liquid chromatograph TRIROTOR (a product of Japan Spectroscopic Co., Ltd.) was used. The detector was UNIDEC-V. A variety of racemates were resolved, with the results shown in Table 1.

TABLE 1

| Racemates | Capacity ratio | | Separation factor | Resolution | Flow rate |
|---|---|---|---|---|---|
| | $k_1'$ | $k_2'$ | $\alpha$ | Rs | ml/min |
| Ph-CH(OH)-CONH$_2$ | 15.4 | 21.9 | 1.42 | 1.0 | 0.5 |
| cyclobutane-1,2-di(CONHPh) | 3.17 | 4.49 | 1.41 | 0.6 | 0.5 |
| phenyl cyclohexyl ketone | 1.94 | 2.78 | 1.43 | 0.88 | 0.5 |
| Ph-C(=O)-CH(OH)-Ph | 6.23 | 10.3 | 1.65 | 1.82 | 0.5 |

TABLE 1-continued

| Racemates | Capacity ratio $k_1'$ | $k_2'$ | Separation factor $\alpha$ | Resolution Rs | Flow rate ml/min |
|---|---|---|---|---|---|
| (epoxide with two phenyl groups) | 1.13 | 1.81 | 1.60 | 1.47 | 0.5 | solvent: a mixture (9:1) of hexane and 2-propanol

COMPARATIVE EXAMPLE 1

A variety of racemic modifications were optically resolved by using silica gel carrying cellulose triacetate under the same conditions as in case of the curdlan triacetate. Table 2 shows the obtained separation factors $\alpha$.

TABLE 2

| Racemic modifications | Separation factor |
|---|---|
| Ph-CH(OH)-CONH$_2$ | 1.08 |
| Cyclobutane-1,2-bis(CONHPh) | 1.13 |
| 2-phenylcyclohexanone | 1.07 |
| Ph-CO-CH(OH)-Ph | 1.05 |
| Ph$_2$-epoxide | 1.22 |

SYNTHESIS EXAMPLE 3 (Synthesis of α-1,3-glucan triacetate)

1.3 g of α-1,3-glucan triacetate (prepared by extracting α-1,3-glucan from *Laetiporus sulphureus* according to the method described by J. Jelsmais in Thesis, University of Groningen, The Netherlands (1979) and converting it into a triacetate according to the method described by K. Ogawa, K. Okamura, T. Yuie, T. Watanabe, and K. Takeo in Carboydrate Polymers (1983) 3, 287) was dissolved in a mixture of 9 ml of dichloromethane, 3 ml of acetic acid, and 4 ml of acetic anhydride, to which was then added 0.05 ml of 7% perchloric acid and the mixture was kept with stirring at 55° C. for 30 minutes to reduce the viscosity. After cooling, the formed solution was neutralized with 0.2 ml of pyridine and then poured into 100 ml of ethanol. The formed precipitate was filtered, washed and dried. From the infrared spectrum, the product could be identified reasonably as α-1,3-glucan triacetate. An intrinsic viscosity thereof, measured in a mixture of dichloromethane and methanol at a ratio of 9:1, was 0.65 at 25° C. A yield was 1.20 g.

EXAMPLE 2

1.1 g of the α-1,3-glucan triacetate synthesized in Synthesis Example 3 was dissolved in a mixture of 8.4 ml of dichloromethane and 0.46 ml of methanol, and the solution was filtered through a glass filter (G3). The filtrate was uniformly mixed with 3.86 g of the silica gel particles prepared in Synthesis Example 1, and the solvent was distilled off in vacuo to obtain a powdery supported resolving agent.

APPLICATION EXAMPLE 2

Several racemic modifications were resolved under the same conditions as in Application Example 1 by using the supported agent obtained in Example 2. Table 2 shows the results.

TABLE 2

| Racemates | Capacity ratio $k_1'$ | Capacity ratio $k_2'$ | Separation factor $\alpha$ | Resolution Rs | Flow rate ml/min |
|---|---|---|---|---|---|
| (structure: diphenyl epoxide) | 1.01 | 3.45 | 3.42 | 3.52 | 0.5 |
| (structure: dimethyl diazine) | 0.31 | >4.67 | >15 | not known | 0.5 |
| (structure: benzoin) | 4.74 | 5.15 | 1.09 | 0.8 | 0.5 |

Solvent: hexane/2-propanol (9:1)

SYNTHESIS EXAMPLE 4 (CURDLAN TRIBENZOATE)

4 g of curdlan triacetate obtained in Synthesis Example 1 was suspended in 8 ml of 2-propanol. Then 3.0 ml of 100% hydrazin hydrate was added to the suspension. The mixture was kept at 70° C. for 4 hours and a half. The resulting curdlan was collected by filtering and washed two times with 2-propanol and then three times with acetone, followed by drying.

1.5 g of the curdlan obtained in the above shown step was treated with 10 ml of benzoyl chloride in 20 ml of dry pyridine at 80° C. for 11 hours. The product was mixed with ethanol to produce precipitates. They were collected with filtration and washed with ethanol. A yield was 4.28 g when dried.

EXAMPLE 3

1.2 g of curdlan obtained in Synthesis Example 4 was dissolved in 7.5 ml of dichloromethane. The solution was filtrated with a G3 glass filter and the filtrate liquid was well mixed with the silica beads obtained in Synthesis Example 1. Then the solvent was removed out at a reduced pressure to obtain a powder of the resolving agent or the carrier.

APPLICATION EXAMPLE 3

(±)-γ-phenyl-γ-butyrolactone was resolved with the resolving agent obtained in Example 3 in the same way as in Application Example 1. An optical isomer having the negative optical activity and having a separation factor of 1.17 was first eluted.

The embodiments of the invention in which an exclusive property or privilege is claimed are defined as follows:

1. A method of separating an optical isomer from a racemic modification thereof, which comprises contacting said racemic modification with a 1,3-glucan derivative, under chromatographic separation conditions effective to separate said optical isomer, said derivative being a compound in which at least 85% of the total hydroxy groups of a 1,3-glucan has been replaced by a substituent which is bonded to said 1,3-glucan by an ester bond, said substituent being selected from the group consisting of aliphatic groups having 2 to 10 carbon atoms, alicyclic groups having 4 to 10 carbon atoms, aromatic groups having 6 to 20 carbon atoms and heteroaromatic groups having 4 to 20 carbon atoms; and recovering said optical isomer.

2. A method as claimed in claim 1, in which said 1,3-glucan derivative is α-1,3-glucan derivative.

3. A method as claimed in claim 1, in which said 1,3-glucan derivative is β-1,3-glucan derivative.

4. A method as claimed in claim 1, in which said 1,3-glucan derivative is free of side chains or is lowly branched.

5. A method as claimed in claim 1, in which the treatment step comprises passing said racemic modification through a chromatographic column or layer under conditions effective for the chromatographic separation of said optical isomer.

6. A method as claimed in claim 1 in which said racemic modification is contacted with curdlan triacetate.

7. The method of claim 6 wherein said optical isomer is selected from the group consisting of

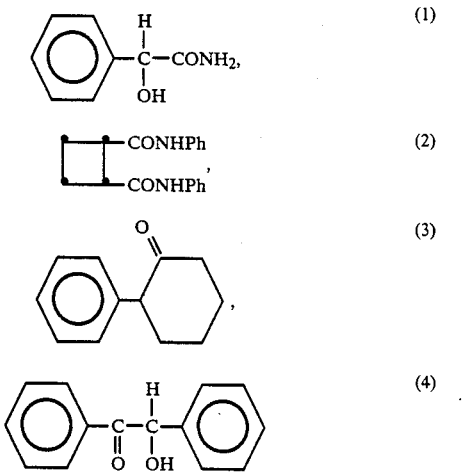

-continued and

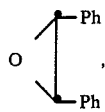 (5)

, wherein Ph stands for phenyl.

8. A method as claimed in claim 1 in which said racemic modification is contacted with curdlan tribenzoate.

9. A method as claimed in claim 1 in which said racemic modification is contacted with α-1,3-glucan triacetate.

10. A method as claimed in claim 1, wherein said substituent has a multiple bond therein.

11. A method as claimed in claim 1 wherein said 1,3-glucan derivative is supported on a carrier of from 1 μm–10 mm in size, having pores of a diameter of from 10 Å–100 μm and is supported on said carrier in an amount of from 1–100 wt. % of the weight of said carrier.

12. A method as claimed in claim 1, wherein said 1,3-glucan derivative is supported on a carrier of from 1 μm–300 μm in size, having pores of 50 Å–50,000 Å in diameter and is supported on said carrier in an amount of from 5–50 wt. % of the weight of said carrier.

* * * * *